United States Patent [19]
Coutts et al.

[11] Patent Number: 6,060,516
[45] Date of Patent: May 9, 2000

[54] N¹-PROPARGYLHYDRAZINES, N²-PROPARGYLHYDRAZINES AND THEIR ANALOGS FOR THE TREATMENT OF DEPRESSION, ANXIETY AND NEURODEGENERATION

[75] Inventors: Ronald Coutts; Glen Baker; Duff Sloley; Jacqueline Shan, all of Edmonton; Peter K. T. Pang, Sherwood Park, all of Canada

[73] Assignee: CV Technologies, Inc., Alberta, Canada

[21] Appl. No.: 09/024,113

[22] Filed: Feb. 17, 1998

[51] Int. Cl.$^7$ .................................................. A61R 31/045
[52] U.S. Cl. ............................................ 514/727; 564/313
[58] Field of Search .............................. 564/313; 514/727

[56] References Cited

U.S. PATENT DOCUMENTS 3,213,138  10/1965  Biel et al. ................................. 260/569
3,359,316  12/1967  Biel et al. ............................. 260/570.8

OTHER PUBLICATIONS

Chem Abstracts 191:603466; rn 61944–48–7; Darbinyan et al, 1981.
Bielstein Abstract of GMELIN registry No. 959297; Baum, Marc M.; Edward H.; J. Chem Soc., Perkin Trans. 1; (1993) 2513–2520; JCPRB4; English; Jun., 1993.

*Primary Examiner*—Samuel Barts
*Attorney, Agent, or Firm*—Arent Fox Kintner Plotkin & Kahn, PLLC

[57] ABSTRACT

The present invention is directed to novel N¹-propargylhydrazines, N²-propargylhydrazines and their salts in pharmaceutical compositions. The compounds according to the present invention have at least one of the following activities: monoamine oxidase-A inhibiting, monoamine oxidase-B inhibiting, anti-depressant, anti-anxiety and neuroprotectant activities. These compounds are useful as monoamine oxidase inhibitors and should be useful for the treatment of depression, anxiety and of neurodegenerative diseases such as Parkinson's disease and Alzheimer's disease.

6 Claims, No Drawings

$N^1$-PROPARGYLHYDRAZINES, $N^2$-PROPARGYLHYDRAZINES AND THEIR ANALOGS FOR THE TREATMENT OF DEPRESSION, ANXIETY AND NEURODEGENERATION

FIELD OF THE INVENTION

The present invention is directed to $N^1$-propargylhydrazines, $N^2$-propargylhydrazines and their salts in pharmaceutical compositions. The compounds according to the present invention have at least one of the following activities monoamine oxidase-A inhibiting, monoamine oxidase-B inhibiting, anti-depressant, anti-anxiety and neuroprotectant activities. These compounds are useful as antidepressants, anxiolytics monoamine oxidase inhibitors and for the treatment of neurodegenerative diseases such as Parkinson's disease and Alzheimer's disease.

RELATED ART

Neither the $N^1$-propargylhydrazines nor $N^2$-propargylhydrazines listed here have been used as monoamine oxidase-A inhibiting, monoamine oxidase-B inhibiting, anti-depressant, anti-anxiety or neuroprotective compounds.

N-Propargyl-N-methylalkylamines have been used as selective monoamine oxidase-B inhibiting and neuroprotective compounds (Birkmayer et al., Journal of Neurotransmission 64 (1985) pages 113–127; Yu et al., Journal of Medicinal Chemistry Volume 35 (1992), pages 3705–3713; Yu et al., Journal of Neurochemistry 63 (1994) pages 1820–1828). However, the activity of the compounds according to the present invention would not have been predicted from the activity of N-propargyl-N-methylalkylamines.

BRIEF SUMMARY OF THE INVENTION $N^1$-Propargyl-substituted hydrazine compounds and $N^2$-propargyl-substituted hydrazine compounds having the following two general formulae:

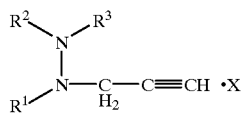

A

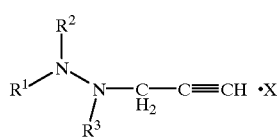

B wherein $R^1$ is selected from the group consisting of H; alkyl $C_1$–$C_8$; alicyclic $C_1$–$C_8$; hydroxylated alkyl $C_1$–$C_8$; phenyl; phenylalkyl $C_1$–$C_8$; ring substituted phenyl preferably substituted with a substituent selected from the group consisting of OH, $CH_3$, $OCH_3$, Cl, Br, F, and $CF_3$; ring substituted phenylalkyl $C_1$–$C_8$ preferably substituted with a substituent selected from the group consisting of OH, $CH_3$, $OCH_3$, Cl, Br, F, and $CF_3$; aryl; ring substituted aryl preferably substituted with a substituent selected from the group consisting of OH, $CH_3$, $OCH_3$, Cl, Br, F, and $CF_3$; arylalkyl $C_1$–$C_8$; ring substituted arylalkyl $C_1$–$C_8$ preferably substituted with a substituent selected from the group consisting of OH, $CH_3$, $OCH_3$, Cl, Br, F, and $CF_3$; arylalkenyl $C_1$–$C_8$; aryl—C=O—alkyl $C_1$–$C_8$; and aryl—O—alkyl $C_1$–$C_8$;

$R^2$ is selected from the group consisting of H; alkyl $C_1$–$C_8$; arylalkyl $C_1$–$C_8$; $COCH_3$; $COCH_2R$ where R is selected from the group consisting of alkyl $C_1$–$C_8$, aryl, and ring substituted aryl preferably substituted with a substituent selected from the group consisting of OH, $CH_3$, $OCH_3$, Cl, Br, F, and $CF_3$;

$R^3$ is selected from the group consisting of H; alkyl $C_1$–$C_8$; arylalkyl $C_1$–$C_8$; $COCH_3$; $COCH_2R$ where R is selected from the group consisting of alkyl $C_1$–$C_8$, aryl, and ring substituted aryl preferably substituted with a substituent selected from the group consisting of OH, $CH_3$, $OCH_3$, Cl, Br, F, and $CF_3$;

and X when present is a salt-forming acid, wherein all alkyl groups are straight chained or branched, all alkenyl groups are straight chained or branched unsaturated alkyl, and the aryl groups are preferably selected from the group consisting of naphthyl, 1,2,3,4-tetrahydronaphthyl, indoyl, furyl, pyridyl, pyrrole and various tricyclic rings, have been found to have useful therapeutic activity as monoamine oxidase inhibiting, anti-depressant, anti-anxiety and/or neuroprotective agents. The compounds are usually but not necessarily isolated in the form of their mono- or di-salt, the salt-forming acids preferably being selected from hydrochloric acid, hydrobromic acid, tartaric acid, maleic acid and oxalic acid.

These compounds have been found to have at least one of the following biological activities: monoamine oxidase inhibiting, anti-depressant, anti-anxiety and neuroprotectant activities.

DETAILED DESCRIPTION OF THE INVENTION $N^1$-Propargyl-substituted hydrazine compounds and $N^2$-propargyl-substituted hydrazine compounds have been found to have useful therapeutic activity as monoamine oxidase inhibiting, anti-depressant, anti-anxiety and/or neuroprotective agents. The compounds are usually but not necessarily isolated in the form of their mono- or di-salt. The salt-forming acids are preferably selected from hydrochloric acid, hydrobromic acid, tartaric acid, maleic acid and oxalic acid. The compounds have the following two general formulae:

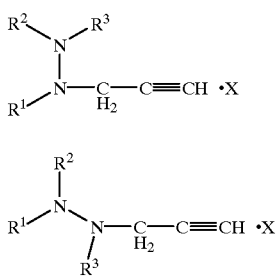

A

B wherein

R¹ is selected from the group consisting of H; alkyl $C_1$–$C_8$; alicyclic $C_1$–$C_8$; hydroxylated alkyl $C_1$–$C_8$; phenyl; phenylalkyl $C_1$–$C_8$; ring substituted phenyl preferably substituted with a substituent selected from the group consisting of OH, $CH_3$, $OCH_3$, Cl, Br, F, and $CF_3$; ring substituted phenylalkyl $C_1$–$C_8$ preferably substituted with a substituent selected from the group consisting of OH, $CH_3$, $OCH_3$, Cl, Br, F, and $CF_3$; aryl; ring substituted aryl preferably substituted with a substituent selected from the group consisting of OH, $CH_3$, $OCH_3$, Cl, Br, F, and $CF_3$; arylalkyl $C_1$–$C_8$; ring substituted arylalkyl $C_1$–$C_8$ preferably substituted with a substituent selected from the group consisting of OH, $CH_3$, $OCH_3$, Cl, Br, F, and $CF_3$; arylalkenyl $C_1$–$C_8$; aryl—C=O—alkyl $C_1$–$C_8$; and aryl—O—alkyl $C_1$–$C_8$;

R² is selected from the group consisting of H; alkyl $C_1$–$C_8$; arylalkyl $C_1$–$C_8$; $COCH_3$; $COCH_2R$ where R is selected from the group consisting of alkyl $C_1$–$C_8$, aryl, and ring substituted aryl preferably substituted with a substituent selected from the group consisting of OH, $CH_3$, $OCH_3$, Cl, Br, F, and $CF_3$;

R³ is selected from the group consisting of H; alkyl $C_1$–$C_8$; arylalkyl $C_1$–$C_8$; $COCH_3$; $COCH_2R$ where R is selected from the group consisting of alkyl $C_1$–$C_8$, aryl, and ring substituted aryl preferably substituted with a substituent selected from the group consisting of OH, $CH_3$, $OCH_3$, Cl, Br, F, and $CF_3$;

and X when present is a salt-forming acid, wherein all alkyl groups are straight chained or branched, all alkenyl groups are straight chained or branched unsaturated alkyl, and the aryl groups are preferably selected from the group consisting of napthyl, 1,2,3,4-tetrahydronapthyl, indoyl, furyl, pyridyl, pyrrole and various tricyclic rings.

The compounds according to the present invention can be prepared by any suitable method including the following method.

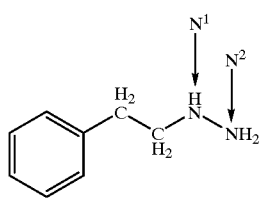

Phenelzine [PLZ]

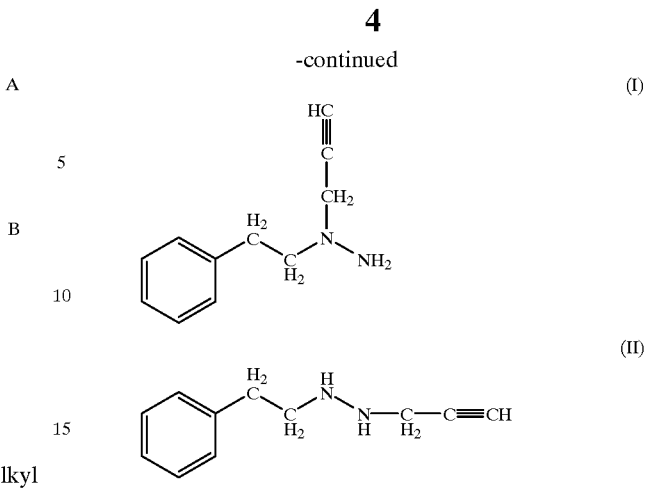

$N^1$-Propargyl-substituted hydrazines (I) and $N^2$-propargyl-substituted hydrazines (II) can be prepared directly from phenelzine [1-(2-phenyl) ethylhydrazine; PLZ] by reaction with propargyl bromide. Phenelzine is reacted with a molar equivalent of propargyl bromide in acetonitrile with excess potassium carbonate at room temperature for 24 hours. A mixture of products ($N^1$-substituted; $N^2$-substituted and $N^1,N^2$-disubstituted) is obtained, though this reaction prefers the production of $N^1$-propargylhydrazine. The resulting material is then filtered and dried. Chromatography on silica gel is used to purify the desired product.

$N^2$-Propargylpheneizine can be prepared by reacting phenelzine in 1 N aqueous NaOH with $(Boc)_2O$. The mixture is stirred at room temperature for 30 minutes. The mixture is extracted with chloroform, dried over sodium sulphate and the solvent removed. The residue is chromatographed on silica gel (ethyl acetate:hexane, 1:2) to provide $N^2$-Boc phenelzine (yield 33%) and $N^1$-Boc phenelzine (yield 66%). The $N^2$-Boc phenelzine is then dissolved in tetrahydrofuran and sodium hydride and propargyl bromide are added to the solution. The mixture is stirred at room temperature overnight. The solid precipitate is filtered out and the filtrate evaporated. The residue is chromatographed on silica gel (ethyl acetate:hexane, 1:8) to provide pure $N^2$-propargyl-$N^2$-Boc phenelzine. The pure $N^2$-propargyl-$N^2$-Boc phenelzine is mixed with 4N HCl in dioxane at room temperature for 1 hour. The solvent is removed and the residue washed 3 times with chloroform. The final product is chromatographed on silica gel (ethyl acetate:hexane, 1:5) to provide $N^2$-propargylphenelzine.

$N^1$-Propargyl-$N^2$-acetylphenelzine can be prepared by reacting $N^1$-propargylphenelzine with 2 molar equivalents acetic anhydride in pyridine. The resulting material is diluted in ethyl acetate, washed with acid, and purified by chromatography on silica gel.

The following three compounds were prepared as described above.

Compound Code# CVT-P039

Chemical Name: $N^2$-propargylphenelzine

Formula: $C_{11}H_{14}N_2$

Molecular Weight: 174

Structure:

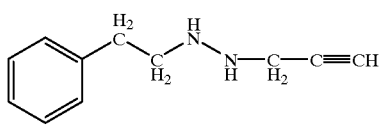

Compound Code# CVT-P040
Chemical Name: $N^1$-propargylphenelzine
Formula: $C_{11}H_{14}N_2$
Molecular Weight: 174
Structure:

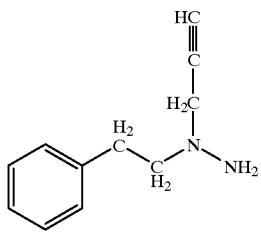

Compound Code# CVT-P041
Chemical Name: $N^1$-propargyl-$N^2$-acetylphenelzine
Formula: $C_{13}H_{16}N_2O$
Molecular Weight: 216
Structure:

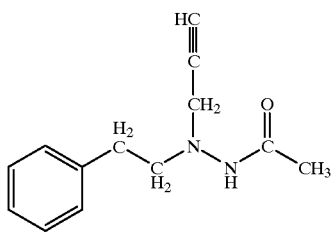

The biological activity of the compounds can be initially determined in vitro. Suitable doses for testing for the ability to inhibit monoamine oxidase-A and monoamine oxidase-B include concentrations of $1\times10^{-4}$ and $1\times10^{-5}$ M. If the substance is active at these doses, a dose response relation is constructed and the effective dose ($ED_{50}$) determined. If the compound proves to be a potent monoamine oxidase inhibitor in vitro it should be tested ex vivo for monoamine oxidase inhibiting activity, ex vivo for GABA elevating activity, ex vivo for serotonin, dopamine and noradrenaline elevating activity, ex vivo for 5-hydroxyindoleacetic acid reducing activity, ex vivo for protection against DSP4 induced depletion of noradrenaline and in vitro for serotonin uptake inhibiting activity. If toxicity is encountered with the initial dose, the dose should be reduced until one is reached which is tolerated by the animals being tested.

Compounds of the general formula I and 11 have been found to possess at least one of the following activities: monoamine oxidase inhibiting, amine elevating, 5-hydroxyindoleacetic acid reducing and neuroprotectant activity and are devoid of GABA elevating activity. These compounds are useful monoamine oxidase inhibitors and may be useful as antidepressants and for the treatment of neurodegenerative diseases such as Parkinson's disease and Alzheimer's disease.

The route of administration includes but is not limited to oral, intravenous, intramuscular, intraperitoneal, and intrathecal. Pharmaceutically acceptable excipients which can be used as a vehicle for the delivery of the compounds will be apparent to those skilled in the art. The dosage of administration is contemplated to be in the range of about 0.001–200 μmol per kg/per day, and preferably about 0.01–10 μmol per kg/per day.

The foregoing embodiments of the present invention are further described in the following Examples. However, the present invention is not limited by the Examples, and variations will be apparent to those skilled in the art without departing from the scope of the present invention.

EXAMPLE 1

Monoamine Oxidase-A Inhibiting Activity In Vitro

The compounds were evaluated for in vitro monoamine oxidase-A inhibiting activity using the radiochemical procedure of Lyles, G. A. and Callingham, B. A. (1982), In vitro and in vivo inhibition by benserazide of clorgyline-resistant amine oxidases in rat cardiovascular tissues, Biochem. Pharmacol. 31: 1417–1424. Radiolabelled 5-hydroxytryptamine was used as the substrate for monoamine oxidase-A. Various concentrations of the compounds were incubated in appropriately diluted homogenates of rat brain or liver in a 0.2 M potassium phosphate buffer. Incubations proceeded at 37° C. for 10 minutes. Incubation was terminated by the addition of acid and the radiolabelled product (5-hydroxyindoleacetic acid) was extracted and quantified by liquid scintillation counting procedures. Incubations were done in triplicate and incubations containing phenelzine were included for comparison. The percent inhibition of monoamine oxidase-A activity compared to controls without the compounds of the present invention was calculated. Results using rat brain and liver homogenates are summarized in Table 1.

TABLE 1

In vitro inhibition of rat brain monoamine oxidase-A by various concentrations of N-propargylhydrazines.

| | | % inhibition of monoamine oxidase A | | | | |
|---|---|---|---|---|---|---|
| CVT # | Tissue | $1 \times 10^{-4}$M | $1 \times 10^{-5}$M | $1 \times 10^{-6}$M | $1 \times 10^{-7}$M | $1 \times 10^{-8}$M |
| phenelzine.$H_2SO_4$ | brain | 100 | 100 | 98.9 | 62.9 | 6.9 |
| CVT-P039.HCl | brain | 31.6 | −25.8 | N.D. | N.D. | N.D. |
| CVT-P040.HCl | brain | 99.5 | 99.1 | 71.1 | 20.6 | 0.7 |
| CVT-P041.HCl | brain | 79.5 | 27.7 | 4.2 | 1.8 | 0.3 |

TABLE 1-continued

In vitro inhibition of rat brain monoamine oxidase-A by various concentrations of N-propargylhydrazines.

| CVT # | Tissue | % inhibition of monoamine oxidase A | | | | |
|---|---|---|---|---|---|---|
| | | $1 \times 10^{-4}$M | $1 \times 10^{-5}$M | $1 \times 10^{-6}$M | $1 \times 10^{-7}$M | $1 \times 10^{-8}$M |
| CVT-P046.HCl | brain | 100 | 99.4 | 49.4 | 18.5 | −5.0 |
| CVT-P047.HCl | brain | 99.7 | 78.2 | 15.9 | −3.8 | −2.9 |

N.D.=not done
CVT-P046 is $N^1$-propargylbenzylhydrazine and CVT-P047 is $N^1$-propargylphenylhydrazine.
CVT-P039, CVT-P040, and CVT-PO41 are as discussed above.

EXAMPLE 2

Monoamine Oxidase-A Inhibiting Activity Ex Vivo

The compounds were evaluated for ex vivo monoamine oxidase-A inhibiting activity using the radiochemical procedure of Lyles, G. A. and Callingham, B. A. (1982). In vitro and in vivo inhibition by benserazide of clorgyline-resistant amine oxidases in rat cardiovascular tissues. Biochem. Pharmacol. 31: 1417–1424. Radiolabelled 5-hydroxytryptamine was used as a substrate for monoamine oxidase-A. The compounds of interest were either injected intraperitonealy in DMSO or administered by gavage in water for various periods. The animals were killed by decapitation and the brains and livers immediately removed and frozen until assayed for monoamine oxidase-A activity. Tissues were homogenized and appropriately diluted in buffer prior to incubation. Incubations proceeded at 37° C. for 10 minutes. Incubation was terminated by the addition of acid and the radiolabelled product (5-hydroxyindoleacetaldehyde and 5-hydroxyindoleacetic acid) was extracted and quantified by liquid scintillation counting procedures. Incubations were done in triplicate and incubations containing phenelzine were included for comparison. The percent inhibition of monoamine oxidase-A activity compared to controls containing no drug was calculated. Results using rat brain and liver homogenates are summarized in Table 2.

TABLE 2

Ex vivo inhibition of rat brain and liver monoamine oxidase-A by various treatments with $N^1$-propargyl phenelzine (CVT-P040).

| Compound | Dose | n | Route | Tissue | % Inhibition Monoamine Oxidase-A |
|---|---|---|---|---|---|
| Control | 0 μmol/kg, 5 hr | 7 | i.p. in 10% DMSO | brain | 0.3 ± 2.9 |
| CVT-P040 | 0.58 μmol/kg, 5 hr | 6 | i.p. in 10% DMSO | brain | 7.2 ± 5.1 |
| CVT-P040 | 5.75 μmol/kg, 5 hr | 8 | i.p. in 10% DMSO | brain | 9.1 ± 4.9 |
| CVT-P040 | 57.5 μmol/kg, 5 hr | 6 | i.p. in 10% DMSO | brain | 86.6 ± 6.7** |
| CVT-P040 | 173 μmol/kg, 5 hr | 4 | i.p. in 10% DMSO | brain | 98.4 ± 0.1** |
| Phenelzine | 5.75 μmol/kg, 5 hr | 6 | i.p. in 10% DMSO | brain | 9.1 ± 5.3 |
| Deprenyl | 5.75 μmol/kg, 5 hr | 6 | i.p. in 10% DMSO | brain | −0.6 ± 1.1 |
| Control | 0 μmol/kg, 5 hr | 5 | i.p. in 10% DMSO | brain | 2.6 ± 8.8 |
| CVT-P040 | 150 μmol/kg, 5 hr | 5 | i.p. in 10% DMSO | brain | 96.7 ± 0.6** |
| CVT-P041 | 150 μmol/kg, 5 hr | 2 | i.p. in 10% DMSO | brain | 98.4 ± 0.0** |
| Phenelzine | 150 μmol/kg, 5 hr | 5 | i.p. in 10% DMSO | brain | 97.2 ± 0.6** |
| Control | 0 μmol/kg, 5 hr | 7 | i.p. in 10% DMSO | liver | −0.5 ± 2.6 |
| CVT-P040 | 0.58 μmol/kg, 5 hr | 6 | i.p. in 10% DMSO | liver | −6.1 ± 4.4 |
| CVT-P040 | 5.75 μmol/kg, 5 hr | 8 | i.p. in 10% DMSO | liver | 43.7 ± 5.4** |
| CVT-P040 | 57.5 μmol/kg, 5 hr | 6 | i.p. in 10% DMSO | liver | 91.7 ± 2.3** |
| CVT-P040 | 173 μmol/kg, 5 hr | 4 | i.p. in 10% DMSO | liver | 97.7 ± 0.3** |
| Phenelzine | 5.75 μmol/kg, 5 hr | 6 | i.p. in 10% OMSO | liver | 36.4 ± 5.3** |
| Deprenyl | 5.75 μmol/kg, 5 hr | 6 | i.p. in 10% DMSO | liver | 8.0 ± 2.2 |
| Control | 2 × vehicle | 5 | per os | brain | 0.0 ± 9.5 |
| CVT-P040 | 2 × 75 μmol/kg | 5 | per os | brain | 96.9 ± 0.8** |
| CVT-P041 | 2 × 75 μmol/kg | 5 | per os | brain | 92.9 ± 1.7** |
| Phenelzine | 2 × 75 μmol/kg | 5 | per os | brain | 96.5 ± 1.2** |
| Control | 2 × vehicle | 5 | per os | liver | 0.1 ± 7.2 |

TABLE 2-continued

Ex vivo inhibition of rat brain and liver monoamine oxidase-A by various treatments with $N^1$-propargyl phenelzine (CVT-P040).

| Compound | Dose | n | Route | Tissue | % Inhibition Monoamine Oxidase-A |
|---|---|---|---|---|---|
| CVT-P040 | 2 × 75 μmol/kg | 5 | per os | liver | 95.4 ± 0.7** |
| CVT-P041 | 2 × 75 μmol/kg | 5 | per os | liver | 98.3 ± 0.2** |
| Phenelzine | 2 × 75 μmol/kg | 5 | per os | liver | 97.7 ± 0.3** |

Values are the mean ± the standard error based on (n) determinations.
Oral doses were administered as 75 μmol/kg on day 1, 75 μmol/kg on day 2 and the animals were killed 5 hours later.
*Significantly different from controls, $p < 0.05$; **Significantly different from controls, $p < 0.01$.

EXAMPLE 3

Monoamine Oxidase-B Inhibiting Activity In Vitro

The compounds were evaluated for in vitro monoamine oxidase-B inhibiting activity using the radiochemical procedure of Lyles, G. A. and Callingham, B. A. (1982). In vitro and in vivo inhibition by benserazide of clorgyline-resistant amine oxidases in rat cardiovascular tissues. Biochem. Pharmacol. 31: 1417–1424. Radiolabelled β-phenylethylamine was employed as a substrate for monoamine oxidase-B. Various concentrations of the compounds of interest were incubated in appropriately diluted homogenates of rat brain or liver in a 0.2 M potassium phosphate buffer. Incubations proceeded at 37° C. for 10 minutes. Incubation was terminated by the addition of acid and the radiolabelled product (phenylacetaldehyde and phenylacetic acid) was extracted and quantified by liquid scintillation counting procedures. Incubations were done in triplicate and incubations containing phenelzine were included for comparison. The percent inhibition of monoamine oxidase-B activity compared to controls containing no drug was calculated. Results using rat brain and liver homogenates are summarized in Table 3.

EXAMPLE 4

Monoamine Oxidase-B Inhibiting Activity Ex Vivo

The compounds were evaluated for ex vivo monoamine oxidase-B inhibiting activity using the radiochemical procedure of Lyles, G. A. and Callingham, B. A. (1982). In vitro and in vivo inhibition by benserazide of clorgyline-resistant amine oxidases in rat cardiovascular tissues. Biochem. Pharmacol. 31: 1417–1424. Radiolabelled β-phenylethylamine was employed as a substrate for monoamine oxidase-B. The compounds of interest were either injected intraperitoneally in DMSO or administered by gavage in water for various periods. The animals were killed by decapitation and the brains and livers immediately removed and frozen until assayed for monoamine oxidase-B activity. Tissues were homogenized and appropriately diluted in buffer prior to incubation. Incubations proceeded at 37° C. for 10 minutes. Incubation was terminated by the addition of acid and the radiolabelled product (phenylacetic acid) was extracted and quantified by liquid scintillation counting procedures. Incubations were done in triplicate and incubations containing phenelzine were included for comparison. The percent inhibition of monoamine oxidase-B activity compared to controls containing no drug was calculated. Results using rat brain and liver homogenates are summarized in Table 4.

TABLE 3

In vitro inhibition of rat brain monoamine oxidase-B by various concentrations of N-propargylhydrazines

| CVT # | Tissue | % inhibition of monoamine oxidase B | | | | |
|---|---|---|---|---|---|---|
| | | $1 \times 10^{-4}M$ | $1 \times 10^{-5}M$ | $1 \times 10^{-6}M$ | $1 \times 10^{-7}M$ | $1 \times 10^{-8}M$ |
| phenelzine.H$_2$SO$_4$ | brain | 100 | 100 | 90.1 | 18.3 | 6.9 |
| CVT-P039.HCl | brain | 20.9 | −0.2 | N.D. | N.D. | N.D. |
| CVT-P040.HCl | brain | 99.7 | 97.9 | 88.8 | 59.8 | 19.9 |
| CVT-P041.HCl | brain | 92.7 | 71.3 | 28.8 | 6.2 | −2.0 |
| CVT-P046.HCl | brain | 100 | 92.3 | 86.2 | 64.9 | 18.6 |
| CVT-P047.HCl | brain | 100 | 94.3 | 65.1 | 17.9 | 0.1 |

N.D. = not done
CVT-P046 is $N^1$-propargylbenzylhydrazine and CVT-P047 is $N^1$-propargylphenylhydrazine.
CVT-P039, CVT-P040, and CVT-P041 are as discussed above.

TABLE 4

Ex vivo inhibition of rat brain and liver monoamine oxidase-B by various treatments with $N^1$-propargylphenelzine (CVT-P040).

| Compound | Dose | n | Route | Tissue | % Inhibition Monoamine Oxidase-A |
|---|---|---|---|---|---|
| Control | 0 μmol/kg, 5 hr | 7 | i.p. in 10% DMSO | brain | 4.0 ± 3.7 |
| CVT-P040 | 0.58 μmol/kg, 5 hr | 6 | i.p. in 10% DMSO | brain | −4.7 ± 2.0 |
| CVT-P040 | 5.75 μmol/kg, 5 hr | 8 | i.p. in 10% DMSO | brain | 11.8 ± 5.1 |
| CVT-P040 | 57.5 μmol/kg, 5 hr | 6 | i.p. in 10% DMSO | brain | 66.1 ± 6.9** |
| CVT-P040 | 173 μmol/kg, 5 hr | 4 | i.p. in 10% DMSO | brain | 93.2 ± 0.8** |
| Phenelzine | 5.75 μmol/kg, 5 hr | 6 | i.p. in 10% DMSO | brain | −2.7 ± 5.6 |
| Deprenyl | 5.75 μmol/kg, 5 hr | 6 | i.p. in 10% DMSO | brain | 42.0 ± 9.9** |
| Control | 0 μmol/kg, 5 hr | 5 | i.p. in 10% DMSO | brain | 0.9 ± 5.9 |
| CVT-P040 | 150 μmol/kg, 5 hr | 5 | i.p. in 10% DMSO | brain | 85.5 ± 1.7** |
| CVT-P041 | 150 μmol/kg, 5 hr | 2 | i.p. in 10% DMSO | brain | 77.6 ± 0.4** |
| Phenelzine | 150 μmol/kg, 5 hr | 5 | i.p. in 10% DMSO | brain | 83.3 ± 2.3** |
| Control | 0 μmol/kg, 5 hr | 7 | i.p. in 10% DMSO | liver | 1.6 ± 2.8 |
| CVT-P040 | 0.58 μmol/kg, 5 hr | 6 | i.p. in 10% DMSO | liver | 1.1 ± 5.4 |
| CVT-P040 | 5.75 μmol/kg, 5 hr | 8 | i.p. in 10% DMSO | liver | 29.3 ± 2.8** |
| CVT-P040 | 57.5 μmol/kg, 5 hr | 6 | i.p. in 10% DMSO | liver | 64.0 ± 5.5** |
| CVT-P040 | 173 μmol/kg, 5 hr | 4 | i.p. in 10% DMSO | liver | 87.9 ± 1.0** |
| Phenelzine | 5.75 μmol/kg, 5 hr | 6 | i.p. in 10% OMSO | liver | 18.1 ± 5.8** |
| Deprenyl | 5.75 μmol/kg, 5 hr | 6 | i.p. in 10% DMSO | liver | 63.7 ± 2.0** |
| Control | 2 × vehicle | 5 | per os | brain | 0.0 ± 4.6 |
| CVT-P040 | 2 × 75 μmol/kg | 5 | per os | brain | 85.4 ± 2.1** |
| CVT-P041 | 2 × 75 μmol/kg | 5 | per os | brain | 73.6 ± 2.2** |
| Phenelzine | 2 × 75 μmol/kg | 5 | per os | brain | 76.4 ± 3.4** |
| Control | 2 × vehicle | 5 | per os | liver | 0.0 ± 5.2 |
| CVT-P040 | 2 × 75 μmol/kg | 5 | per os | liver | 82.3 ± 2.3*** |
| CVT-P041 | 2 × 75 μmol/kg | 5 | per os | liver | 97.4 ± 0.2** |
| Phenelzine | 2 × 75 μmol/kg | 5 | per os | liver | 95.6 ± 1.0** |

Values are the mean ± the standard error based on (n) determinations.
Oral doses were administered as 75 μmol/kg on day 1, 75 μmol/kg on day 2 and the animals were killed 5 hours later.
*Significantly different from controls $p < 0.05$; **Significantly different from controls, $p < 0.01$
***Significantly different from controls and other treatments, $p < 0.01$.

EXAMPLE 5

Prevention of DSP-4 Neurotoxicity Ex Vivo

Neuroprotectant activity was evaluated by examining the prevention of DSP-4 induced noradrenaline depletion in mouse hippocampus as described in Yu, P. H., Davis, B. A., Fang, J. and Boulton, A. A. (1994), Neuroprotective effect of some monoamine oxidase-B inhibitors against DSP-4 induced noradrenaline depletion in the mouse hippocampus, J. Neurochem. 63: 1820–1828. Briefly, mice were injected (i.p.) with either 20% DMSO or potential neuroprotectants (10 mg/kg in 20% DMSO). One hour later they were injected with either water or DSP-4 (50 mg/kg in water). One week later the mice were killed and the brains removed and the hippocampus dissected out. The hippocampus was frozen and saved for estimation of noradrenaline and other aminergic neurotransmitters and their metabolites as in Sloley, B. D. and Goldberg J. I. (1991), Determination of γ-glutamyl conjugates of monoamines by means of high-performance liquid chromatography with electrochemical detection and application to gastropod tissues, J. Chromatog. 567: 49–56. The rest of the brain was frozen and retained for estimation of monoamine oxidase activities ex vivo as described earlier. Administration of CVT-P040, like (−)-deprenyl significantly protected against DSP-4 induced noradrenaline depletion (Table 6). Furthermore CVT-P040 demonstrated a strong preference for MAO-A inhibition in these circumstances. CVT-P041 did not exhibit a neuroprotective effect.

TABLE 5

Protection against noradrenaline depletion in mouse hippocampus produced by DSP-4.

| First Treatment | Second Treatment | n | NA ng/g | % NA Restoration | MAO-A % Inhibition | MAO-B % Inhibition |
|---|---|---|---|---|---|---|
| 20% DMSO | Saline | 5 | 350 ± 17 | n/a | 0.4 ± 1.5 | 0.0 ± 5.6 |
| (−)-deprenyl 10 mg/kg | DSP-4 50 mg/kg | 5 | 315 ± 34 | 86.6 | 18.8 ± 6.0* | 64.8 ± 2.5* |
| CVT-P040 10 mg/kg | DSP-4 50 mg/kg | 5 | 235 ± 26 | 55.4 | 57.9 ± 2.9* | 20.3 ± 2.2* |
| 20% DMSO | DSP-4 50 mg/kg | 5 | 93 ± 21* | n/a | −4.0 ± 10.7 | 1.6 ± 6.8 |
| Saline | Saline | 5 | 493 ± 73 | n/a | 0.0 ± 6.6 | 0.9 ± 6.4 |

TABLE 5-continued

Protection against noradrenaline depletion in mouse hippocampus produced by DSP-4.

| First Treatment | Second Treatment | n | NA ng/g | % NA Restoration | MAO-A % Inhibition | MAO-B % Inhibition |
|---|---|---|---|---|---|---|
| (−)-deprenyl 10 mg/kg | DSP-4 50 mg/kg | 5 | 432 ± 13 | 73.1 | 9.9 ± 6.0 | 52.3 ± 3.0 |
| CVT-P041.HCl 10 mg/kg | DSP-4 50 mg/kg | 5 | 168 ± 31* | −43.2 | 4.3 ± 6.2 | −3.7 ± 9.4 |
| Saline | DSP-4 50 mg/kg | 5 | 266 ± 42* | n/a | −1.4 ± 3.2 | −6.1 ± 3.0 |

Values are the means ± the standard errors based on n determinations. n/a not applicable.
*Significantly different from vehicle treated animals.

EXAMPLE 6

Dose Response of the Effect of CVT-P040 on Rat Hypothalamus Amine and Amine Metabolite Concentrations and Comparison to Phenelzine and (−)-deprenyl The effects of various doses of CVT-P040 on the concentrations of hypothalamus amine neurotransmitters and their metabolites were evaluated by examining concentrations of noradrenaline (NA), dopamine (DA), 5-hydroxytryptamine (5-HT), 5-hydroxyindoleacetic acid (5-HIAA) and 3,4-dihydroxyphenylacetic acid (DOPAC) in rat hypothalami 5 hours after the injection of the drug. Briefly, rats were injected with CVT-P040 (0.58, 5.75, 57.5 or 150 μmol/kc), vehicle, (−)-deprenyl (5.75 μmol/kg) or phenelzine (5.75 or 150 μmol/kg) and killed 5 hours later. The brains were removed and divided in half. One half of the brain was frozen in isopentane on dry ice and retained for estimates of amino acid neurotransmitter concentrations. The other half had the hypothalamus removed and frozen on dry ice for later estimates of amines and their metabolites according to the method of Sloley, B. D. and Goldberg J. I. (1991), Determination of γ-glutamyl conjugates of monoamines by means of high-performance liquid chromatography with electrochemical detection and application to gastropod tissues, J. Chromatog. 567: 49–56. The rest of the brain was frozen on dry ice for ex vivo examination of MAO activity as described earlier. CVT-P040 significantly elevated 5-HT and NA concentrations and significantly reduced 5-HIAA and DOPAC concentrations in a dose dependent manner (Table 7). The reduction in 5-hydroxyindoleacetic acid concentrations was comparable to that determined with equivalent doses of phenelzine.

TABLE 6

Effects of various intraperitoneal or oral doses of $N^1$-propargylphenelzine (CVT-P040).
$N^1$-propargyl-$N^2$-acetylphenelzine (CVT-P041), phenelzine and (−)-deprenyl
on brain noradrenaline (NA), dopamine (DA), 5-hydroxytryptamine (5-HT),
5-hydroxyindoleaceticacid (5-HIAA) and 3,4-dihydroxyphenylacetic acid
(DOPAC)concentrations in rat hypothalamus

| Compound | Dose | n | NA ng/g | DA ng/g | 5-HT ng/g | 5-HIAA ng/g | DOPAC ng/g |
|---|---|---|---|---|---|---|---|
| | ip | | | | | | |
| Control | 0 μmol/kg, 5 hr | 7 | 1240 ± 146 | 733 ± 61 | 759 ± 41 | 468 ± 47 | 90 ± 5 |
| CVT-P040 | 0.58 μmol/kg, 5 hr | 6 | 1155 ± 81 | 716 ± 82 | 652 ± 69 | 350 ± 28* | 77 ± 9 |
| CVT-P040 | 5.75 μmol/kg, 5 hr | 8 | 1332 ± 98 | 717 ± 85 | 634 ± 58 | 327 ± 26** | 80 ± 6 |
| CVT-P040 | 57.5 μmol/kg, 5 hr | 6 | 1672 ± 82* | 753 ± 99 | 1324 ± 102** | 294 ± 22** | 49 ± 13* |
| CVT-P040 | 173 μmol/kg, 5 hr | 4 | 1867 ± 253* | 865 ± 19 | 1509 ± 146** | 148 ± 10** | 30 ± 7** |
| Phenelzine | 5.75 μmol/kg, 5 hr | 6 | 1468 ± 119 | 544 ± 66 | 755 ± 53 | 334 ± 23* | 89 ± 7 |
| Deprenyl | 5.75 μmol/kg, 5 hr | 6 | 1510 ± 70 | 541 ± 44 | 821 ± 44 | 407 ± 22 | 87 ± 9 |
| Control | 0 μmol/kg, 5 hr | 5 | 1462 ± 216 | 358 ± 52 | 665 ± 48 | 338 ± 28 | 72 ± 8 |
| CVT-P040 | 150 μmol/kg, 5 hr | 5 | 2050 ± 202* | 522 ± 28 | 1497 ± 111** | 131 ± 8** | 45 ± 4* |
| CVT-P041 | 150 μmol/kg, 5 hr | 5 | 2141 ± 86* | 461 ± 34 | 1100 ± 39** | 179 ± 6** | 91 ± 6 |
| Phenelzine | 150 μmol/kg, 5 hr | 5 | 2113 ± 102* | 385 ± 20 | 1583 ± 95** | 131 ± 16** | 51 ± 4 |
| | per os | | | | | | |
| Control | 2 × vehicle | 5 | 1286 ± 87 | 406 ± 59 | 665 ± 32 | 279 ± 29 | 82 ± 8 |
| CVT-P040 | 2 × 75 μmol/kg | 5 | 2230 ± 101++ | 487 ± 47 | 1215 ± 36++ | 197 ± 8+ | 50 ± 3+ |
| CVT-P041 | 2 × 75 μmol/kg | 5 | 1749 ± 91+ | 553 ± 129 | 946 ± 115+ | 228 ± 17 | 50 ± 4+ |
| Phenelzine | 2 × 75 μmol/kg | 5 | 2148 ± 171++ | 607 ± 103 | 1232 ± 87++ | 167 ± 26+ | 54 ± 4+ | per os: animals received 75 pmol/kg on day 1, 75 pmol/kg on day 2 and were killed 5 hours later. Values are the mean ± the standard error based on (n) determinations.
*Significantly different from controls $p < 0.05$
**Significantly different from controls $p < 0.01$
+Significantly different from controls $p < 0.05$
++Significantly different from controls and CVT-P041 $p < 0.05$

EXAMPLE 7

Dose Response of the Effect of CVT-P040 and CVT-P041 on Brain Gamma-aminobutyric Acid Concentrations and Comparison to Phenelzine Effects of various doses of CVT-P040, CVT-P041 and phenelzine on the concentrations of some brain amino acids were evaluated by examining concentrations of gamma-aminobutyric acid (GABA) 5 hours after the injection of the drug. Briefly, rats were injected with CVT-P040 (150 pmol/kg), vehicle, or phenelzine (150 µmol/kg) and killed 3 or 5 hours later. The brains were removed and divided in half. One half of the brain was frozen in isopentane on dry ice and retained for estimates of GABA concentrations. GABA and other amino acid concentrations were estimated using the method of Wong, J. T. F., Baker, G. B. and Coutts, R. T. (1990), A rapid, sensitive assay for γ-aminobutyric acid in brain using electron-capture gas chromatography, Res. Comm. Chem. Path. Pharmacol. 70: 115–122.

CVT-P040 and CVT-P041 did not elevate GABA concentrations at doses as high as 150 µmol/kg (Table 7). In contrast, phenelzine (150 pmol/kg) caused elevations in brain GABA concentrations. In addition, phenelzine elevated alanine levels by about 4 fold. This elevation of alanine was not seen when CVT-P040 or CVT-P041 were administered. Thus CVT-P040 and CVT-P041 lack the GABA and alanine elevating effect known to occur with phenelzine.

TABLE 7

Effects of various doses of $N^1$-propargylphenelzine (CVT-P040). $N^1$-propargyl-$N^2$-acetylphenelzine (CVT-P041) and phenelzine on brain valine, alanine and gamma-aminobutyric acid (GABA) concentrations in rat brain

| Compound | Dose | n | Valine µg/g | GABA µg/g |
|---|---|---|---|---|
| Control | vehicle, 5 hr, ip | 5 | 22.1 ± 0.8 | 280 ± 13 |
| CVT-P040 | 150 µmol/kg, 5 hr, ip | 5 | 22.9 ± 1.4 | 270 ± 23 |
| CVT-P041 | 150 µmol/kg, 5 hr, ip | 2 | 20.6 ± 0.5 | 253 ± 0 |
| Phenelzine | 150 µmol/kg, 5 hr, ip | 5 | 22.9 ± 0.4 | 773 ± 37* |
| Control | 2 × 75 µmol/kg, per os | 5 | 27.1 ± 2.5 | 340 ± 48 |
| CVT-P040 | 2 × 75 µmol/kg, per os | 5 | 25.4 ± 1.8 | 329 ± 43 |
| CVT-P041 | 2 × 75 µmol/kg, per os | 5 | 26.4 ± 1.4 | 300 ± 22 |
| Phenelzine | 2 × 75 µmol/kg, per os | 5 | 24.3 ± 0.8 | 733 ± 64* | per os: animals received 75 µmol/kg on day 1, 75 µmol/kg on day 2 and were killed 5 hours later. Values are the mean ± the standard error based on (n) determinations.
*Significantly different from controls p < 0.01

EXAMPLE 8

Neurotrophic Effects of CVT-P040 on PC12 Cell Growth

The effects of CVT-P040 on neurite outgrowth in cell culture were investigated using an established PC 12 pheochromocytoma cell culture. The effects of CVT-P040 and nerve growth factor on neurite outgrowth were estimated using the method described by Rydel, R. E and Greene, L. A.(1987), Acidic and basic fibroblast growth factors promote stable neurite outgrowth and basic neuronal differentiation in cultures of PC12 cells, J. Neuroscience 7: 3639–3653. Briefly, PC12 cells were seeded and maintained in 100 cm$^2$ tissue culture dishes at 37° C. in RPMI1640 media containing 1% antibiotics, 10% heat inactivated horse serum and 5% fetal bovine serum in a water saturated atmosphere of 95% air and 5% $CO_2$. The cells were mechanically dislodged and plated into 35 mm collagen-coated tissue culture dishes containing a total of 2.0 ml complete medium at a density of 1–10$^4$ cells/ml. The medium was changed 3 times/week. Cellular responses to CVT-P040 and nerve growth factor (NGF) were determined by counting the number of PC12 cells containing processes. Photographs of the cells were taken after seven days treatment. Two cell fields were chosen in each dish and the photographs developed and printed. The cells and neurites were assessed as follows: cells which are circular and demonstrate no neurite outgrowth score 0 (S0); cells which are elongate or possess a single small outgrowth score 1 (S1); cells with two or more small outgrowths score 2 (S2); cells which possess one or two neurites two times the diameter of the cell body score 3 (S3); cells with more than two long neurites score 4 (S4). The neurite index was calculated using the following formula; Neurite Index=total neurite score (ΣS)/ total cell number (ΣN); ΣS=S1×N+S2×N +S3×N+S4×N, where N is the number of cells in each cell field.

CVT-P040 (100 µM) and NGF (0.1, 0.3 and 1.0 ng/ml) increased neurite outgrowth in PC12 cells (Table 9). Coadministration of CVT-P040 (100 µM) with either 0.3 or 1.0 ng/ml NGF increased the neurite index above those cultures receiving 0.3 or 1.0 ng/ml NGF alone.

TABLE 8

Effect of CVT-P040 and nerve growth factor (NGF) on PC12 neurite outgrowth

| Treatment | n | Index of Neurite Outgrowth |
|---|---|---|
| Control | 6 | 0.19 ± 0.01 |
| CVT-P040 100 µM | 6 | 0.35 ± 0.03* |
| NGF 0.1 ng/ml | 6 | 0.58 ± 0.03* |
| CVT-P040 100 µM, NGF 0.1 ng/ml | 6 | 0.55 ± 0.03* |
| NGF 0.3 ng/ml | 6 | 0.79 ± 0.07* |
| CVT-P040 100 µM, NGF 0.3 ng/ml | 6 | 0.97 ± 0.06** |
| NGF 1.0 ng/ml | 6 | 1.16 ± 0.06* |
| CVT-P040 100 µM, NGF 1.0 ng/ml | 6 | 1.53 ± 0.07** |

Values are the means ± the standard errors based on n determinations.
*Significantly different frorn controls p < 0.05.
**Significantly different from controls and from equal concentrations of NGF p < 0.05

EXAMPLE 9

Effects of CVT-P040 on Serotonin (5-hydroxytryptamine, 5-HT) Uptake in vitro CVT-P040 was evaluated for the ability to inhibit serotonin uptake in rat striatal prisms using the procedure of Martin, I. L., Baker, G. B. and Mitchell, P. R. (1978), The effect of viloxazine hydrochloride on the transport of noradrenaline, dopamine, 5-hydroxytryptamine and γ-aminobutyric acid in rat brain tissue Neuropharmacology 17: 421–423. Briefly, untreated rats were killed by guillotine decapitation, their brains removed, placed on an ice-cooled plate and the striatum was dissected out from the rest of the brain. The striatum was then chopped into 0.1×0.1×2 mm prisms using a McIlwain tissue chopper and suspended in 5 volumes incubation medium containing 123 mM sodium chloride, 5 mM potassium chloride, 2.7 mM calcium chloride, 1.2 mM magnesium sulphate, 20 mM TRIS-HCl buffer (pH 7.5), 1 mM ascorbic acid, 10 mM glucose and 12.5 μM nialamide. The suspension was stored out of direct light and buried in ice. Aliquots (1 ml) of the tissue suspension were added to flasks containing 4 ml of incubation medium and this mixture was incubated for 15 min at 37° C. in a shaking water bath. Next, 10 pi of the appropriate chemical was added to each tube except the blanks and controls, followed by the addition of 10 μl of $^3$H-5-HT (final concentration 0.1 μM). The mixtures were incubated for 5 min at 37° C., then quickly filtered with a Millipore vacuum filter apparatus and rinsed two times with 5 ml warm (37° C.) incubation medium. Filters were transferred to scintillation vials and 10 ml Ready Safe scintillation cocktail was added to each. Radioactive content per tube was counted using a liquid scintillation spectrophotometer. Percent 5-HT uptake inhibition was calculated by applying the following equation:

$$\% \text{ inhibition} = 100 - \left[ \frac{(\text{mean of sample} - \text{mean of blank})}{(\text{mean of controls} - \text{mean of blank})} \times 100 \right]$$

TABLE 9

Effect of CVT-P040, CVT-P041 and other analogues on serotonin uptake in vitro.

| Compound Tested | % Inhibition |
| --- | --- |
| Fluoxetine (1 × 10$^4$M) | 93.2 ± 3.5 |
| CVT-P040 (1 × 10$^{-4}$M) | 90.1 ± 3.3 |
| CVT-P041 (1 × 10$^{-4}$M) | 22.2 ± 4.6 |
| CVT-P046 (1 × 10$^{-4}$M) | 48.9 ± 2.6 |
| CVT-P047 (1 × 10$^{-4}$M) | 32.5 ± 4.5 |
| Fluoxetine (1 × 10$^{-5}$M) | 79.9 ± 8.6 |
| CVT-P040 (1 × 10$^{-5}$M) | 50.2 ± 2.5 |

TABLE 9-continued

Effect of CVT-P040, CVT-P041 and other analogues on serotonin uptake in vitro.

| Compound Tested | % Inhibition |
| --- | --- |
| Fluoxetine (1 × 10$^{-6}$M) | 67.7 ± 5.4 |
| CVT-P040 (1 × 10$^{-6}$M) | 49.1 ± 4.3 |

CVT-P046 is N$^1$-propargylibenzylhydrazine, CVT-P047 is N$^1$-propargylphenylhydrazine

We claim:
1. An N$^1$-propargylhydrazine derivative having the following general formula A:

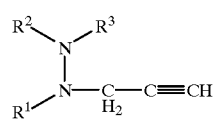

wherein
R$^1$ is phenylalkyl C$_1$–C$_8$;
R$^2$ is H; and
R$^3$ is H;
and pharmaceutically acceptable salts thereof, wherein said N$^1$-propargylhydrazine derivative is N$^1$-propargylphenelzine.

2. A pharmaceutical composition comprising the N$^1$-propargylhydrazine derivative according to claim 1 in combination with a pharmaceutically acceptable carrier.

3. A method for inhibiting monoamine oxidase activity, comprising administering a monoamine oxidase activity inhibiting amount of an N$^1$-propargylhydrazine derivative according to claim 1 to a patient in need of such treatment.

4. The method according to claim 3, wherein said N$^1$-propargylhydrazine derivative has anti-depressant, anti-anxiety and/or neuroprotective activity.

5. The method according to claim 3, wherein said N$^1$-propargylhydrazine derivative is administered orally, as an injection or transdermally.

6. A method for treating neurodegenerative diseases comprising administering an amount of an N$^1$-propargylhydrazine derivative according to claim 1 effective to treat said neurodegenerative disease to a patient in need of such treatment.

* * * * *

UNITED STATES PATENT AND TRADEMARK OFFICE
CERTIFICATE OF CORRECTION

PATENT NO. : 6,060,516

DATED : May 9, 2000

INVENTOR(S) : Ronald COUTTS et al.

It is certified that error appears in the above-identified patent and that said Letters Patent is hereby corrected as shown below:

Column 2, line 13, change ``aryl-C=O-alkyl'' to --aryl-CO-alkyl--.

Column 6, line 5, change ``11'' to --II--.

Column 17, line 40 change ``(1x10$^4$M)'' to --(1x10$^{-4}$M).

Signed and Sealed this

Twenty-second Day of May, 2001

Attest:

NICHOLAS P. GODICI

Attesting Officer    Acting Director of the United States Patent and Trademark Office